United States Patent [19]

Lucast et al.

[11] Patent Number: 5,613,942
[45] Date of Patent: Mar. 25, 1997

[54] ADHESIVE SHEET MATERIAL SUITABLE FOR USE ON WET SURFACES

[75] Inventors: Donald H. Lucast, North St. Paul; Clyde D. Calhoun, Stillwater; John E. Riedel, Hugo; Charles W. Taylor, Lake Elmo, all of Minn.

[73] Assignee: Minnesota Mining and Manufacturing Company, St. Paul, Minn.

[21] Appl. No.: 317,854

[22] Filed: Oct. 4, 1994

[51] Int. Cl.$^6$ ..................................................... A61F 13/00
[52] U.S. Cl. ............................. 602/52; 602/44; 602/45; 602/59; 604/307
[58] Field of Search ............................. 602/41, 42, 43, 602/44, 45, 47, 52, 54, 58, 59; 604/304, 307, 387

[56] References Cited

U.S. PATENT DOCUMENTS

| | | | |
|---|---|---|---|
| Re. 24,906 | 12/1960 | Ulrich | 206/59 |
| 3,121,021 | 2/1964 | Copeland | 117/122 |
| 3,307,545 | 3/1967 | Surowitz | 602/47 |
| 3,331,728 | 7/1967 | Lane | 602/47 |
| 3,457,919 | 7/1969 | Harbard | 602/55 |
| 3,483,018 | 12/1969 | Waldman | 117/68.5 |
| 3,507,943 | 4/1970 | Such et al. | 264/103 |
| 3,528,417 | 9/1970 | Gardner | 602/47 |
| 3,579,628 | 5/1971 | Glander et al. | 424/28 |
| 3,645,835 | 2/1972 | Hodgson | 161/146 |
| 3,972,328 | 8/1976 | Chen | 128/156 |
| 3,975,350 | 8/1976 | Hudgin et al. | 260/30.4 N |
| 4,112,177 | 9/1978 | Salditt et al. | 428/304 |
| 4,148,958 | 4/1979 | Tischer et al. | 428/196 |
| 4,181,127 | 1/1980 | Linsky et al. | 128/155 |
| 4,226,915 | 10/1980 | Iijima et al. | 428/492 |
| 4,337,772 | 7/1982 | Roeder | 128/290 R |
| 4,490,425 | 12/1984 | Knoke et al. | 428/90 |
| 4,511,615 | 4/1985 | Ohta | 428/198 |
| 4,559,938 | 12/1985 | Metcalfe | 128/156 |
| 4,595,001 | 6/1986 | Potter et al. | 128/156 |
| 4,772,499 | 9/1988 | Greenway | 428/43 |
| 4,798,201 | 1/1989 | Rawlings et al. | 128/156 |
| 4,814,365 | 3/1989 | Takiyama et al. | 523/514 |
| 4,844,973 | 7/1989 | Konishi et al. | 428/286 |
| 5,010,883 | 4/1991 | Rawlings et al. | 128/155 |
| 5,012,801 | 5/1991 | Feret | 128/155 |
| 5,027,803 | 7/1991 | Scholz et al. | 128/89 |
| 5,242,726 | 9/1993 | Pariseau | 428/40 |
| 5,244,457 | 9/1993 | Karami | 602/55 |
| 5,308,313 | 5/1994 | Karami | 602/55 |
| 5,409,472 | 4/1995 | Rawlings | 602/55 X |
| 5,441,056 | 8/1995 | Weber | 128/849 |

FOREIGN PATENT DOCUMENTS

| | | | |
|---|---|---|---|
| 0091800 | 4/1983 | European Pat. Off. | A61L 15/06 |
| 2-45582 | 2/1990 | Japan | C07J 7/02 |
| 1280631 | 7/1972 | United Kingdom | C09J 7/02 |

OTHER PUBLICATIONS

Dahlquist, C.A., "Adhesion An Interdisciplinary Science," *Interdisciplinary Science Review*, 2, 2 (1977).

*Adhesives Age*, Mar., 1982.

"The Manmade Fibers, " *Encyclopedia of Textiles*, 3rd Edition, pp. 1–69, by the Editors of American Fabrics and Fashions Magazine, Prentice–Hall, Inc., Englewood Cliff, NJ. 1980, particularly pp. 66–69.

Labarthe, J., "Manufactured Fiber Families," *Elements of Textiles*, MacMillan Publishing Co., Inc., NY, NY (1975) Chapter 4.

Labarthe, J., "Fabric Constructions," *Elements of Textiles*, Macmillan Publishing Company, Inc., NY, NY (1975) Chapter 6.

PSTC–1 Peel Adhesion Test, *Test Methods for Pressure Sensitive Tapes*, 7th Edition, developed by the Specifications and Technical Committee of the Pressure Sensitive Tape Council, Glenview, IL, Copyright 1976.

"Tenderm™ for Sensitive Skin," LecTec Corporation, 1990.

"LecTec Makes Its Mark," *Converting Magazine*, Aug. 1988.

*Primary Examiner*—Corrine M. McDermott
*Assistant Examiner*—Chalin Smith
*Attorney, Agent, or Firm*—Gary L. Griswold; Walter N. Kirn; Robert W. Sprague

[57] ABSTRACT

This invention relates to an adhesive sheet material, such as an adhesive tape, which is suitable for use on wet surfaces, in particular upon wet skin. The adhesive sheet material effectively binds to the wet surface and moves moisture away from the surface. The adhesive sheet material has a porous backing having opposing sides and is made of non-wettable fibers. The water-insoluble pressure sensitive adhesive is discontinuously coated on one side of the backing to provide areas of the adhesive interspersed with areas of bare backing.

14 Claims, No Drawings

ADHESIVE SHEET MATERIAL SUITABLE FOR USE ON WET SURFACES

FIELD OF THE INVENTION

This invention relates to an adhesive sheet material, such as an adhesive tape, which is suitable for use on wet surfaces, in particular upon wet skin. The adhesive sheet material effectively bonds to the wet surface and transports moisture away from the surface.

BACKGROUND OF THE INVENTION

Adhesive sheet materials for use in general industry, packaging, and medicine/surgery are wellknown and highly developed. These materials are composed of a backing and a coating of pressure sensitive adhesive (PSA) which are selected so as to provide an appropriate balance of the desirable properties for adhesive sheet materials: adhesion and elasticity. In addition, such properties as peel strength and creep resistance are often considered. These properties of adhesive materials have been reviewed by Dahlquist in *Interdisciplinary Science Review*, 2, 2 (1977) and more recently in *Adhesives Age*, March, 1982, incorporated herein by reference.

Typically, adhesive sheet materials or tapes are designed with selected variations of the foregoing properties so that the sheet or tape will effectively adhere to the targeted surface. For example, a sheet or tape for adhering packages will exhibit high cohesion and adhesion but low stretchiness and elasticity. The peel strength for such a packaging tape will be low but the shear strength and creep resistance will be high.

A paper binding tape will generally exhibit high adhesion but practically no elasticity. It will have a relatively high shear strength. Its tack will be high so that low pressure will cause it to adhere.

A sheet or tape for use on living skin will exhibit moderate adhesion and moderate to high stretchiness and elasticity. The cohesive strength of such a sheet or tape should be high enough so that no PSA residue will remain on the skin when the tape is removed. This sheet or tape will also exhibit a high tack so that moderate pressure will cause adhesion.

The presence of a fluid between the sheet or tape and the surface to which it is to adhere will typically cause adhesion failure. Water and other nonadherent substances, such as oil, are well-known vexations to anyone trying to apply tape to skin. The physical barrier posed by the fluid prevents the PSA from binding to the surface. Since such fluid covered surfaces are a perennial problem when using adhesive sheets and tapes, much research has been devoted to the solution.

"Breathable" and "absorbent" adhesive tapes for combatting this problem are commercially available and have been extensively described in the patent literature. For example, Copeland in U.S. Pat. No. 3,121,021 describes a breathable surgical tape made of a nonwoven backing and microporous layer of PSA. The microporous PSA layer allows water vapor to pass through.

A different technique is described by Gander in U.S. Pat. No. 3,579,628. Gander discloses a dressing film in which the film-backing absorbs water vapor and the water acts as a plasticizer for the polymer composing the film. The film is self-adherent when wet.

Film absorption of water is also addressed by Potter in European Patent Application 0 091 800. Potter describes an adhesive surgical film in which the PSA is pattern coated onto the film. The film is water vapor absorptive.

Rawlings has further developed the absorptive reservoir concept in U.S. Pat. No. 5,010,883. Rawlings describes a multilayer adhesive coated sheet material in which the adhesive coated layer is perforated for transmission of liquid water. The surface layer is a continuous vapor transmissive film. Liquid water is transported into a reservoir region between the two layers and slowly evaporates as vapor from the surface layer.

These improvements in adhesive sheet materials or tapes, however, are designed to handle slight amounts of moisture. They cannot handle significant quantities of liquid water. In addition, the absorptive capacities of PSA's and backings typically used for such "absorbent" sheets and tapes limit the amount of moisture vapor that can be removed from the surface. Finally, the adherent ability of such sheets and tapes is poor when applied to wet surfaces. Consequently, at present, no adhesive sheet material or tape is available for use on extremely wet surfaces. In particular, no known adhesive sheet material or tape can effectively be used under water or upon a surface such as skin that has been thoroughly wetted with a stream of water. As a result, there is a need to develop an adhesive sheet material or tape which is suitable for use under extremely wet conditions. A further need exists for the development of such a sheet material or tape which will bind to an extremely wet surface such as skin covered with water or immersed in water.

SUMMARY OF THE INVENTION

The present invention is directed to an adhesive sheet material or tape which is suitable for use in adhering to a wet surface. The adhesive sheet material is made of a porous backing having opposing sides and a pressure sensitive adhesive (PSA) coated on one side of the backing. The PSA coating is discontinuous so as to provide areas of PSA interspersed with areas of bare backing.

The backing is a nonwoven, knitted or woven construction of fibers that are substantially non-water absorptive. The non-absorbent character of the fibers is a function of the fiber composition. Fibers useful in the present invention have an ability to absorb no more than about 4 percent by weight water; preferably, no more than about 3 percent by weight water. Because of this character, water can pass unimpeded through the backing.

The PSA is water insoluble and relatively non-absorbent. The amount of PSA coated per unit area of the entire backing (i.e., coated and uncoated areas) is moderate to heavy, at least about 2 mg per sq. cm, preferably from about 6 to about 15 mg per sq. cm. This amount allows the adhesive sheet material to adhere well to the surface when the sheet material is used. Preferably, the PSA also has a balance of adhesion and elasticity to enable it to adhere to living skin. Alternatively, these properties of the PSA can also be adjusted to the particular needs of inanimate surfaces.

The coating pattern of PSA on the backing permits efficient movement of surface water into and through the backing when the adhesive sheet material is used. The distance from the middle of a PSA area to a bare backing area is calculated to enable water movement from the PSA to the bare backing in a matter of seconds. The size of the individual areas of PSA coating on the adhesive sheet material is no greater than 5 mm in at least one dimension, preferably from about 0.5 mm to about 5 mm, more preferably about 1 to about 3 mm, and most preferably no greater than 5 mm in either of two dimensions. The total PSA area is from about 30 percent to about 80 percent of the total area of the sheet material, preferably from about 40 to 70 percent. Consequently, the area of the backing which is not coated by adhesive is between about 20 and 70 percent of the area of the backing. The pattern of PSA coating may be dot patterns, stripe patterns, wavy patterns, lines, squares, and other regular or irregular patterns.

The invention is as well directed to a method for adhering an adhesive sheet material to a surface wet with an aqueous fluid such as water. The method includes the step of applying to the wet surface an adhesive sheet material which will move the water away from the surface and through the sheet backing. Through the facilitation of unimpeded water movement through the backing and the short distance between areas of PSA coating and bare backing, the water on the surface is pressed to the outer surface of the backing during adhesive sheet material application. The adhesive sheet material accordingly can be adhered to a surface that is either wet with water or immersed in water.

DETAILED DESCRIPTION OF THE INVENTION

The adhesive sheet material of the present invention displays significant, strong adhesion to surfaces that are thoroughly wetted or covered with water such as by a film of water, flowing water or under water. The adhesive sheet material adheres to surfaces that will continue to be immersed in water, such as by flowing water or a body of water, or that will continue to develop significant amounts of water on their surfaces, e.g. by sweating. The adhesive sheet material of the invention will adhere to dry surfaces as well.

Although it is not meant to be a limitation of the invention, it is believed that these wet adhesion characteristics are achieved by such adhesive sheet material properties as the discontinuous pattern of the PSA on the backing, the water-insoluble and non-absorbent nature of the PSA, the amount of PSA present, the substantially non-water absorptive character of the backing and preferably the porosity of the entire adhesive sheet material. These properties are believed to direct the surface water into and through the backing when the adhesive sheet material is pressed onto a wet surface. The discontinuous pattern and water-insoluble and non-absorbent nature of the PSA are believed to cause water displacement from the surface contacted by the PSA. The application pressure forces the water into and through the backing. The substantially non-water absorptive character of the backing is believed to facilitate the passage of water to the outer surface of the sheet material during the water pumping action caused by pressing the adhesive sheet material on the surface during application. The water-insoluble and nonabsorbent character and amount of PSA are believed to seal the contacted surface so that water cannot re-wet the surface.

The Backing and its Fibers

The backing for the adhesive sheet material is formed of fibers and has a nonwoven, knit or woven construction. The fibers are substantially non-water absorptive, such that they absorb less than about 4 percent by weight water, preferably less than 3 percent by weight water. Functionally, this property means that water will not absorb into or otherwise be held by the fibers. The fibers may be surface treated with a variety of agents (either hydrophobic or hydrophillic) so long as the agents do not render the fibers water absorptive. These properties enable water to move unimpeded through the backing and minimize water absorption or retention by the backing.

The fiber structures useful in the present invention include a multilayer configuration, a coated configuration and a solid homogeneous configuration. These fibers are generally known in the art and are described in Encyclopedia of Textiles, Third Edition, "The Manmade Fibers", pp. 1–69, by the Editors of American Fabrics and Fashions Magazine, Prentice-Hall, Inc., Englewood Cliffs, N.J., 1980, particularly pp. 66–69, the disclosure of which is incorporated herein by reference.

The multilayer fibers preferably have cores composed of one or more polymers selected from a polyolefin, a polyester, a polyamide or a polyurethane and substituted forms thereof wherein the substituents are pendent aprotic groups such as alkyl (preferably of 1 to 6 carbon atoms), aryl (preferably of 6 to 10 carbon atoms), ester and halogen groups (hereinafter "List of Polymers"). The outer layers of the multilayer fibers are also composed of one or more polymers on the List of Polymers and may contain one or more embedded or polymerized hydrophobic agents such as suitable fluorochemicals or silicones.

The coated fibers are composed of cores and coatings. The cores are preferably composed of one or more polymers on the List of Polymers. The coatings are covalently bonded, embedded or adhered films of one or more hydrophobic agents for fibers, such as silicones, fluorocarbons and other water repellant agents (e.g., water and rain repellant agents for carpet and cloth such as "Scotchgard® Brand Water Repellant" sold by 3M, St. Paul, Mn.).

The solid homogeneous fibers can be composed of one or more polymers on the List of Polymers.

The multilayer fibers, the coated fibers and the solid homogeneous fibers can be prepared by solution or emulsion spinning, extrusion and other techniques known in the art for preparing fibers. See, for example, "Elements of Textiles" Jules Labarthe, , MacMillan Publishing Co., Inc., New York, N.Y., 1975, Chapters 4 and 6, the disclosures of which are incorporated herein by reference. Post-formation techniques such as reactive or mechanical/thermal coating or surface layer polymerization can be used to form the multilayer or coated fibers. The solid homogeneous fibers can constitute the cores for the multilayer and coated fibers.

The fibers are formed into the backing using known weaving, knitting or nonwoven techniques. See, for example, "Fabric Constructions" in "Elements of Textiles," Jules Labarthe, MacMillan, (1975) Chapter 6, the disclosure of which is incorporated herein by reference. Knitting or weaving the fibers, filaments of the fibers, or threads composed of the fibers, is effective to produce a knit or woven backing having fibers running in the longitudinal and lateral directions. Mechanical looms and knit or weave racks can be used to produce such knit or woven material.

The nonwoven backing can be produced by melt forming, e.g. spin blowing, or melt blowing, air forming, mechanical forming with bonding by a chemical, thermal or mechanical process or hydroentanglement. These techniques are known and are described in "Elements of Textiles" cited supra, incorporated herein by reference. The fibers are arranged to run in both a longitudinal and a lateral direction.

The Pressure Sensitive Adhesive

The pressure sensitive adhesive (PSA) used according to the invention is composed of a water insoluble and non-absorbent, preferably viscoelastic polymeric, composition. The PSA is also water tolerant, i.e., it continues to function as an adhesive even in the presence of large amounts of water. The PSA also exhibits an adhesion, (as shown by peel strength), a lift (i.e., extent to which adhesive prematurely separates from the surface to which the tape is applied), and a creep resistance (i.e., resistance to flow) which are appropriate for the particular surface under consideration. Generally, selection of amounts and kinds of ingredients to provide appropriate peel strength and lift will depend upon the nature of the targeted surface and the adherence to be accomplished. A moderate peel strength and a low lift are preferred for use with living skin. A high peel strength and a low lift are preferred for use with an inanimate object. For an explanation relating peel strength and lift to kinds and amounts of PSA ingredients, see Kirk Othmer Encyclopedia of Chemical Technology, 4th Ed., New York, N.Y. 1992, Vol. 1 "Adhesives", the disclosure of which is incorporated herein by reference.

The ingredients present in the PSA include a viscoelastic polymer and an optional tackifier. Fillers, antioxidants, stabilizers and cross-linking agents may also be added. The viscoelastic polymer may have tack itself in which case no tackifying ingredient is needed. The viscoelastic polymer may be a polyacrylate, a polyolefin, a polyether, a polyisoprene, a butyl rubber, a natural rubber, a styrene-butadiene rubber, a polyurethane, a polyester and the like. The viscoelastic polymer can be mixtures or blends of these polymers. Tackifying ingredients are known in the art and include, for example, resins, gums, dextrins and the like.

Although the composition for the PSA may include a combination of hydrophobic and hydrophilic ingredients, its overall characteristic must be non-absorbent, water-insoluble and water tolerant. By "non-absorbent" it is meant that the PSA is capable of absorbing no more than about 10 percent by weight water; preferably, no more than about 7 percent by weight water. By "water-insoluble" it is meant that the PSA has a solubility in water of no more than 2 percent by weight; preferably no more than 0.5 percent by weight. The water tolerant characteristic means that the PSA does not dissolve, degrade or disperse in water and its adhesive character is not adversely affected by water.

Methods for Forming Adhesive Sheet Material

The PSA is applied to the backing as a pattern to form the adhesive sheet material according to techniques known in the art. Such techniques include spray application, roller printing, screen printing and similar single contact techniques. For roller printing, a calendering apparatus that contains the desired pattern embossed upon a cylinder can be rolled first through the PSA or a solution of it and then rolled over the backing. The calender has a surface composed of a release agent such as a silicone, a polyperfluoroolefin or other non-stick material so that the PSA will release from the calender and coat the backing. The depressions on the calender row are filled with the solution of PSA and coat a pattern of PSA on the backing. Block, screen and plate printing techniques can be applied like the roller printing technique to directly produce the adhesive sheet material.

One preferred method of application involves screen patterning the PSA onto a release paper and contact or lamination of the coated release paper to the backing. The release paper process can be conducted in continuous or batch techniques. The continuous technique may utilize screen printing, spray printing or other coating methods to apply a pattern of the PSA onto a moving sheet of the release paper followed by lamination of the release paper and the knit, woven or nonwoven backing. The batch technique involves block or plate printing onto such a release paper and subsequent backing lamination. Such release paper techniques are known in the art.

If the PSA is a curable composition, the pre-adhesive composition can be pattern coated onto the backing by spraying, calendering, screen printing and the like. The cure can be achieved by UV radiation or by the addition of a free radical curing agent to the coated pre-adhesive composition.

In another technique, the PSA may be coated from solution in patterns as described above.

Physical Characteristics of the Adhesive Sheet Material

The linear dimensions of the adhesive sheet material may incorporate designs to provide any desired shape and size of the adhesive sheet material. The dimensions may provide a self-wound or linered roll, tape, or any of the following on a release liner: a sheet, a patch, a plug, a pad, a label, a string, a line, a custom shaped design, rectangular sheets that can be cut to any size and shape and any similar adherent or taping material. The thickness of the sheet material is limited only by practical concerns such as bulk and capability of the sheet material to dry.

The adhesive sheet material of the present invention is porous owing to its composition, its knit, woven or nonwoven character and the pattern coating of the adhesive. The porosity of the entire adhesive sheet material is such that its Gurley value is preferably in the range of 0 to 15 sec per 100 cc air;;, especially preferably less than 2 sec per 100 cc air as measured on a Gurley Densometer Model 4110 according to ASTM D726-58 Method A.

The physical characteristics of the adhesive sheet material of the invention include flexibility and high conformability to irregular surfaces.

The peel strength (measure of adhesion) property of the adhesive sheet material can be varied according to the parameters desired for the specific application. Use of appropriate combinations of backing strength, tightness of knit, weave or tufting in the backing and the appropriate adhesive character for the PSA can be selected by known techniques to achieve the desired variation in this property. For example, to adhere to skin, an adhesive sheet material will have a peel strength of at least about 25 grams per inch of width (i.e., about 0.1 Newtons per cm of width).

Embodiments

In one embodiment of the present invention, an adhesive sheet material can be prepared from a nonwoven spunbonded web of solid polypropylene fibers. This backing can be prepared according to methods well known to those skilled in the art (see, for example, "Elements of Textiles" (supra)) and is commercially available as "Lutrasil® Brand Spunbond Nonwoven Fabric" from Freudenberg Spunweb Co., Durham, N.C. The backing has a thickness of about 0.2 to 2 mm. The coating for this embodiment is a PSA composed of a self-tacky, viscoelastic polyacrylate, e.g., as described by Ulrich in U.S. Pat. No. Re 24,906, incorporated herein by reference. The polyacrylate PSA is coated onto the backing in an amount of at least about 2 mg per sq. cm, preferably about 6 to 15 mg per sq. cm of backing, and as dots or circles having a radius of no more than about 1 mm with no more than 5 mm (preferably no more than 1 mm) of bare backing between the dots.

To prepare this embodiment of the adhesive sheet material, the PSA can be coated on a metal plate containing an embossed negative relief pattern of dots of dimension mentioned above. The PSA in this pattern can be transferred to a silicone release paper and the release paper applied by lamination to the nonwoven backing to form the adhesive sheet material.

Other preferred embodiments are made from backings of nonwoven webs composed of rayon, polyester, polyamide or polyolefin fibers or blends of these fibers which are coated with a non-water absorbent agent such as a water repellant fluorochemical coating agent, a fluorinated polymer or a polysilicone. The non-water absorbent agent can be bound or embedded in the surface layer of the melt spun fibers or can be surface applied to any of the nonwoven webs. See, for example, the disclosure of U.S. Pat. No. 5,027,803 which is incorporated by reference. These backings can be pattern coated with a water-insoluble, non-absorbent PSA such as a polyacrylate ester, a viscous polyolefin with tackifier or other similar hydrophobic PSA. The pattern coating of PSA for these embodiments can be constructed of strips of PSA approximately 0.1 to 1 mm width with 0.1 to 1 mm spaces between and about 6 to 15 mg of PSA per sq. cm of backing.

Applications

The adhesive sheet materials and tapes of the present invention can be used for both medical and nonmedical or industrial uses. These uses are especially desirable where the surfaces to be taped or bound are in extremely wet environments. It is generally found that a sheet material or tape of the present invention will strongly adhere to a wet surface after a few seconds of finger pressure to cause the PSA to force the water away from the surface. Generally, the initial peel strength of the sheet or tape will be at least 0.1 Newtons/cm of width, preferably, about 0.15 to 0.20 Newtons/cm of width.

The following examples provide further illustrations of the invention. These examples, however, are not meant to be limitations of the invention which is fully described by the foregoing general text.

EXAMPLE 1

Preparation and Comparison of a Dot Pattern PSA Tape

A dot pattern PSA tape was prepared by printing a tackified synthetic block copolymer of butadiene and styrene pressure sensitive adhesive onto a rayon/polyester nonwoven backing. The tape parameters are as follows.
  a. The backing was a commercially available hydroentangled rayon/polyester nonwoven backing, "HEF 703-2" (available from International Paper, Veratec Nonwovens Group, Walpole, Mass.) having the following specifications:
    i. backing width of 20 cm (8 inches);
    ii. backing thickness of approximately 0.1 to 0.2 mm;
    iii. backing porosity of 0.1 sec. per 100 cc air (Gurley value); and
    iv. a water absorbency of less than about 2 percent by weight.
  b. The PSA was an adhesive prepared by mixing at 300° F. (149° C.) of a blend consisting of 25 parts "Kraton™ 1112 Rubbers" (a rubbery block copolymer of butadiene and styrene available from Shell Chemical Company, Houston, Tex.), 55 parts "Wingtack Plus™ Hydrocarbon Resins" (a hydrocarbon resin tackifier available from Goodyear Tire and Chemical Corp., Akron, OH) and 20 parts "Tufflo™ Process Oil 6056 Mineral Oil" (available from Lyondell Petrochemical Co., Houston, Tex.) having Tg of 260.5° K.

The printing was accomplished by a conventional rotary screen printing technique. The parameters for printing included:
  a. an adhesive application temperature of 150°–155° C;
  b. a 20 mesh screen for rotary printing to provide a PSA dot pattern of 20 mesh;
  c. a printing rate of 15–16 meters per minute; and,
  d. an application of 7.95 to 8.37 mg of PSA per sq. cm backing.

The dot pattern PSA tape was evaluated dry and on the skin of the backs of six human volunteers which had been wetted with dripping paper towels. Commercially available "Micropore® brand surgical tape" (3M) was also evaluated for a side-by-side comparison. The results of these evaluations are shown below and are reported as an average:

TABLE I

| Tape | T-0[1] | T-24[2] | Lift[3] | Residue[4] | T-0-Wet[5] |
| --- | --- | --- | --- | --- | --- |
| Dot Pattern PSA Tape | 0.853 | 0.768 | 2.4 | 1.1 | 0.205 |
| Micropore ® Tape | 0.127 | 0.533 | 2.0 | 0.0 | 0.062 |

[1] The T-0 is the adhesion of the dry tape to a dry surface at time zero (upon application) as measured according to the following Skin Adhesion Protocol. The adhesion is measured in force per unit width as Newtons per centimeter.
[2] T-24 is the adhesion of the dry tape to a dry surface at 24 hours as measured according to the following Skin Adhesion Protocol. The adhesion is measured in force per unit width as Newtons per cm.
[3] Lift is measured according to the following protocol.
[4] Residue is measured according to the following protocol.
[5] T-0 wet is the adhesion of the tape to a wet surface at time zero as measured according to the following Skin Adhesion Protocol. The units are Newtons per centimeter.

The data showed that the combination of printed discontinuous coating, hydrophobic PSA, and non-wettable backing gave a usefully high adhesion to wet skin.

PROTOCOLS

Skin Adhesion

Evaluation of the adhesiveness of a composition to human skin is an inherently temperamental determination. Human skin possesses wide variations in composition, topography, and the presence/absence of various body fluids. However, comparative average values of adhesion are attainable by using test results from tapes from several individuals as described herein.

Initial skin adhesion ($T_0$), skin adhesion after 24 hours of continuous contact with the skin ($T_{24}$), and skin adhesion to wet skin ($T_{WET}$) are measured in accordance with the widely accepted PSTC-1 Peel Adhesion Test for single coated adhesive tape conducted at a removal angle of 180°. The PSTC-1 Peel Adhesion Test (incorporated herein by reference) is a testing protocol established by the Specifications and Technical Committee of the Pressure Sensitive Tape Council located at 5700 Old Orchard Road, Skokie, Ill. The test is modified for our purposes by applying the tape to the skin of a living human.

Three samples measuring 2.5 cm wide by 7.6 cm long are applied to the back of each of six human subjects (three men and three women). The subjects are placed in a prone position with arms at their sides and heads turned to one side. Samples are applied to both sides of the spinal column with the length of each sample positioned at a right angle to the spinal column. The samples are applied without tension or pulling of skin.

Those samples tested for wet skin adhesion are applied to skin which had been moistened with a water saturated cloth, leaving visually observable drops of standing water, immediately before application of the sample.

The samples are pressed into place with a 2 kg roller moved at a rate of approximately 2.5 cm/sec with a single forward and reverse pass. No manual pressure should be applied to the roller during application.

The samples are then removed either immediately after application ($T_0$) or after 24 hours of continuous contact with the skin ($T_{24}$), at a removal angle of 180° and removal rate of 15 cm per minute, using a conventional adhesion tester equipped with 25 lb (11.3 kg) test line attached to a 2.5 cm clip. The clip is attached to the edge of the sample furthest from the spinal column by manually lifting about 1 cm of the sample from the skin and attaching the clip to the raised edge. The adhesion tester is a strain-gauge mounted on a motor-driven carriage.

The measured force required to effect removal is reported in Newtons per cm. To adhere to wet skin, the T-0-Wet value must be greater than about 0.1 Newtons/cm. Thus, the results of Table I indicate that the tape of the present invention will adhere to wet skin while the standard "Micropore® Tape" will not.

Adhesive Lift

Evaluation of the adhesive tenacity of a composition to human skin is an inherently temperamental determination for the same reasons mentioned above in connection with evaluation of the adhesiveness of a composition to human skin.

However, the observational values as to adhesive tenacity (Lift) are generally reproducible and in accord with subjective assessments of similar properties.

The Adhesive Lift Test is a subjective assessment of the extent to which adhesive tape prematurely separates from the body after application of a sample in accordance with the Skin Adhesion Test. The applied samples are visually inspected just prior to testing for Skin Adhesion (i.e., twenty-four hours after application) to determine the extent to which the edges of the sample have separated from the skin. Each sample is assigned a numerical rating from 0 to 5 based on the following observation:

| Rating | Definition |
|---|---|
| 0 | No visible separation. |
| 1 | Separation at edges of tape only. |
| 2 | Separation of 1% to 25% of tape area. |
| 3 | Separation of 26% to 50% of tape area. |
| 4 | Separation of 51% to 75% of tape area. |
| 5 | Separation of 76% to 100% of tape area. |

Each sample is assigned a single whole number from the list established above by each panel member. The assigned values from the panel members (usually 6 members) are then averaged and reported to the tenths position. Due to the subjective nature of the test, differences of less than 0.5 in averaged residue values should be considered substantially the same. Table I indicates that the tapes of the present invention have lift substantially equivalent to standard tapes for use on human skin.

Adhesive Residue

As with the rating of Adhesive Lift, an assessment of the Adhesive Residue Rating (Residue) of a composition to human skin is an inherently temperamental but reproducible determination.

The Adhesive Residue Test is a subjective assessment of the amount of adhesive left upon the skin after removal of an adhesive sample in accordance with the Skin Adhesion Test. The skin directly underlying each sample was visually inspected to determine the extent to which the area contacted by the adhesive retains residual adhesive. Each sample was then assigned a numerical rating from 0 to 5 based on the following observation:

| Rating | Definition |
|---|---|
| 0 | No visible residue. |
| 1 | Residue at edges of tape only. |
| 2 | Residue covering 1% to 25% of tested area. |
| 3 | Residue covering 26% to 50% of tested area. |
| 4 | Residue covering 51% to 75% of tested area. |
| 5 | Residue covering 76% to 100% of tested area. |

Each sample was assigned a single whole number from the list established above by each panel member. The assigned values from the panel members (usually 6 members) were then averaged and reported to the tenth position. Due to the subjective nature of the test, differences of less than 0.5 in averaged residue values should be considered substantially the same.

Preferred skin adhesives will generally exhibit an average residue rating below about 2.5.

EXAMPLE 2

Dot Pattern PSA Tape with Fluorochemical-coated Fiber Backing

Rayon dot pattern tapes were prepared by rotary screen printing using the adhesive, apparatus and procedure described in Example 1. The backing used was a hydroentangled web of rayon and polyester fibers of the type described in Example 1. The backing had a width of 15 cm, a thickness of about 0.1 to 0.2 mm and a porosity of 0.1 sec per 100 cc air (Gurley value). (This backing is indicated as "703-1" in Table II.)

In another variation backing described above was coated to saturation with 1.6 percent by weight of a fluorinated aliphatic chemical mixture FC-270 (commercially available from the 3M Company, St. Paul, Minn.) followed by ambient drying. (This fluorchemical-coated backing is indicated as "703-1 FC" in Table II.)

In another variation a backing was prepared as above with 1% of a surface coating of the 3M Company fluorochemical "FM 3559." A tape was prepared from this backing according to the procedure, parameters and PSA given above. (Uncoated backing and fluorochemical-coated backing are indicated as "703-2" and "703-2,FC," respectively, in Table II.)

Pattern-coated tapes of the present invention were prepared using the various uncoated and fluorochemical-coated backings described above, according to the procedures described in Example 1. The adhesive was the copolymer described in Example 1, coated at 9.2 mg per sq. cm. of backing.

The following Table provides the results of tests conducted according to the procedures given in Example 1 for the tapes described above and for 3M "Micropore® Tape."

TABLE II

| Backing | T-0-dry | T-24-dry | T-0-wet* |
| --- | --- | --- | --- |
| 703-1 | 0.63 | 0.80 | 0.28 |
| 703-1,FC | 0.64 | 0.90 | 0.28 |
| 703-2 | 0.76 | 0.85 | 0.24 |
| 703-2,FC | 0.74 | 0.88 | 0.23 |
| 3M Micropore ® | 0.15 | 0.46 | 0.05 |

*Expressed in Newtons/cm

EXAMPLE 3

Plate Printed Tapes

Pattern-coated pressure sensitive adhesive tapes using several different backings were prepared by a plate printing procedure. The plate was a metal tool with raised ridges (0.2–0.25 mm high, 0.25mm wide) in a square grid pattern having a distance from center to center of the grid squares of 2.5 mm. The plate was coated with a silicone release agent ("Syloff 23" available from Dow Corning Corp., Midland, Mich.) mixed with 7.5% of "Syloff 23A Catalyst 176" (a catalyst available from Dow Corning Corp., Midland, Mich.). The silicone/catalyst mixture was thinned to 6% solids with 50/50 pentane/heptane; painted on the printing plate and cured at 150° C. for 10 to 15 minutes. The coated plate was post-cured at about 25° C. for several hours as described in the instructions for preparing the release agent.

Adhesive was then coated onto the plate and dried at about 25° C. The adhesive consisted of 70% by weight isooctylocrylate, 15% by weight acrylic acid and 15% by weight of an acrylated polyethylene oxide oligomer, commercially available as "Carbowax 750" from Union Carbide Corp., present as 50 percent by weight in a solvent of 60% ethyl acetate, 30% isopropyl alcohol and 10% toluene. Strips of various nonwoven webs were pressed onto the surface and worked into the adhesive with a stiff bristle brush. The nonwoven tape backings used were:

(a) CFX nylon (available from Allied Signal Corp., East Providence, R.I.), (b) polypropylene melt blown web, coated with 5% by weight "Triton X-100" brand octyl phenoxypolyethoxyethanol (available from Union Carbide Chemical and Plastics Co., Danbury Conn.), and (c) a spun fiber web polyethylene coated with 1% "Atmer 685" brand surfactant (available from ICI Americas, Wilmington, Del.).

The strips of discontinuously coated adhesive tape were removed from the plate and applied to the palm of a wet hand by holding in place with pressure for 5 to 10 seconds. After 1 to 2 minutes all of the tapes showed resistance to being peeled off.

Comparative Example 4

A commercially available pattern-coated pressure sensitive adhesive tape was evaluated as described in Example 1, except that the tape was used on only three human subjects. The tape is commercially available from Lectec Corporation, Minnetonka, Minn., as "Superpore™ Tape". The adhesive is an isoprene/styrene elastomer, a rosin ester tackifying resin and a salt of a long-chain fatty acid. The backing consists of polyester and cellulose fibers. The adhesive and backing absorb 147 weight percent water.

The results are reported as an average in Table III.

TABLE III

|  | T-0-dry* | T-24-dry* | T-0-wet* |
| --- | --- | --- | --- |
| Superpore ™ Tape | 0.3 | 0.63 | 0.07 |

*Expressed in Newtons/cm

Table III demonstrates that "Superpore™ Tape" does not have a peel strength when applied to wet skin as high as the tapes of this invention.

We claim:

1. An adhesive sheet material, comprising:
   a porous backing with opposing sides, which is made of fibers which absorb less than about 4 percent by weight water, and
   a water-insoluble, pressure sensitive adhesive which is capable of absorbing no more than about 10 percent by weight water, and which adhesive is discontinuously coated on the backing to provide areas of the pressure sensitive adhesive interspersed with areas of uncoated backing, the areas of backing which are not coated by adhesive being between about 20 and 70 percent of the area of the backing; wherein the porosity of the backing is sufficient to provide the adhesive sheet material with a Gurley value of about 0 to 15 seconds per 100cc of air, and wherein said adhesive sheet material is permeable to liquid water.

2. An adhesive sheet material according to claim 1 wherein the backing is a nonwoven, knitted or woven material.

3. An adhesive sheet material according to claim 1 wherein the amount of pressure sensitive adhesive coating on the backing is at least about 2 mg per sq. cm.

4. An adhesive sheet material according to claim 3 wherein the amount is in a range of from about 6 to about 15 mg per sq. cm.

5. An adhesive sheet material according to claim 1 wherein the areas of the backing coated with adhesive are no greater than about 5 mm in at least one dimension of the coated surface area of the backing.

6. An adhesive material according to claim 5 wherein the areas of the backing coated with adhesive are no greater than about 5 mm in two dimensions of the coated surface area of the backing.

7. An adhesive sheet material according to claim 1 wherein the fibers are selected from the group consisting of multilayer fibers, coated fibers and solid homogeneous fibers.

8. An adhesive sheet material according to claim 7 wherein the fibers are made at least in part of a polymer selected from the group consisting of polyolefin, substituted polyolefin, polyester, substituted polyester, polyamide, substituted polyamide, polyurethane and substituted polyurethane, wherein the substituent of any of the foregoing substituted polymers is an aprotic pendent group.

9. The adhesive sheet material according to claim 7 wherein the fibers are coated fibers and the coating is a fluorochemical or a silicone.

10. An adhesive sheet material according to claim 1 wherein the pressure sensitive adhesive comprises a viscoelastic polymer.

11. An adhesive sheet material according to claim 10 wherein the viscoelastic polymer is a thermoplastic polymer, a cross-linked polymer or a cross-linkable polymer.

12. An adhesive sheet material according to claim 10 wherein the viscoelastic polymer is selected from the group consisting of polyacrylate, polyolefin, polyether, polyisoprene, butyl rubber, natural rubber, polyurethane, polyester, and a block copolymer of butadiene and styrene.

13. An adhesive sheet material, comprising:

a woven, knitted or nonwoven, porous, fibrous backing with opposing sides, which is comprised of fibers selected from the group consisting of multilayer fibers having a surface layer containing a hydrophobic agent, coated fibers having a surface coating of a hydrophobic agent, and solid homogeneous fibers, so that the fibers absorb less than about 4 percent by weight water, and a water-insoluble pressure sensitive adhesive which is capable of absorbing no more than about 10 percent by weight water and which adhesive is discontinuously coated on the backing to provide areas of the adhesive interspersed with areas of bare backing, the areas of pressure sensitive adhesive being of an individual size no greater than about 5 mm in at least one dimension of the coated surface area of the backing, the amount of pressure sensitive adhesive coated on the backing being at least about 2 mg per sq. cm., and the total area coated with pressure sensitive adhesive being 30 to 80 percent of the total area of backing;

wherein the porosity of the backing is sufficient to provide the adhesive sheet material with a Gudey value of about 0 to 15 seconds per 100 cc of air, and wherein said adhesive sheet material is permeable to liquid water.

14. A method for adhering an adhesive sheet material to a surface wet with an aqueous liquid, comprising:

applying to the wet surface the adhesive sheet material under conditions of sufficient time and pressure to cause the aqueous liquid to move through the adhesive sheet material, the adhesive sheet material comprising a porous, fibrous backing having opposing sides, which is made of fibers which absorb less than about 4 percent by weight water; and a water-insoluble pressure sensitive adhesive which is capable of absorbing no more than about 10 percent by weight water and which adhesive is discontinuously coated on the backing, the coating providing areas of pressure sensitive adhesive interspersed with areas of bare backing, the areas of backing which are not coated by adhesive being between 20 and 70 percent of the area of the backing; wherein the porosity of the backing is sufficient to provide the adhesive sheet material with a Gurley value of about 0 to 15 seconds per 100 cc of air and wherein said adhesive sheet material is permeable to liquid water.

\* \* \* \* \*